(12) United States Patent
Danzer et al.

(10) Patent No.: US 8,536,986 B2
(45) Date of Patent: Sep. 17, 2013

(54) MEDICAL EXAMINATION OR TREATMENT DEVICE, IN PARTICULAR X-RAY OR CT DEVICE

(75) Inventors: Uwe Danzer, Kalchreuth (DE); Robert Kagermeier, Nürnberg (DE); Judith Regn, Nürnberg (DE); Anton Schraufstetter, Seukendorf (DE); Dietmar Sierk, Erlangen (DE); Reiner Staab, Balersdorf (DE)

(73) Assignee: Siemens Aktiengesellschaft, München (DE)

( * ) Notice: Subject to any disclaimer, the term of this patent is extended or adjusted under 35 U.S.C. 154(b) by 2084 days.

(21) Appl. No.: 11/430,577

(22) Filed: May 9, 2006

(65) Prior Publication Data

US 2006/0255904 A1    Nov. 16, 2006

(30) Foreign Application Priority Data

May 10, 2005   (DE) .................. 10 2005 021 604

(51) Int. Cl.
   *G08C 19/00*       (2006.01)
(52) U.S. Cl.
   USPC ....................... 340/13.26; 600/427
(58) Field of Classification Search
   USPC ............. 600/407, 427, 300; 340/438, 439, 340/988, 13.26; 128/897
   See application file for complete search history.

(56) References Cited

U.S. PATENT DOCUMENTS

| | | | |
|---|---|---|---|
| 5,826,283 A * | 10/1998 | Edwards ........................ | 4/503 |
| 7,010,369 B2 * | 3/2006 | Borders et al. ............... | 700/90 |
| 2002/0091765 A1 * | 7/2002 | Bocionek ...................... | 709/203 |
| 2003/0195644 A1 | 10/2003 | Borders et al. | |
| 2004/0150525 A1 * | 8/2004 | Wilson et al. ............. | 340/572.1 |
| 2004/0171935 A1 * | 9/2004 | Van Creveld et al. ........ | 600/437 |
| 2006/0165371 A1 | 7/2006 | Zwart | |

FOREIGN PATENT DOCUMENTS

| | | |
|---|---|---|
| DE | 103 25 106 A1 | 12/2004 |
| EP | 1 344 540 A1 | 9/2003 |
| WO | WO 2004036527 A1 | 4/2004 |

OTHER PUBLICATIONS

Communication from Japanese Patent Office stating cited reference, Feb. 16, 2012, pp. 1-2.

* cited by examiner

*Primary Examiner* — Tse Chen
*Assistant Examiner* — Rochelle Reardon

(57) ABSTRACT

Medical examination or treatment device, in particular x-ray or CT device, comprising a control device controlling the operation of one or a number of device elements, as well as at least one mobile control element assigned to the control device, the control element communicating wirelessly with the control device for operating the examination or treatment device to issue control signals, with a detector element for detecting an item of information which can be read out or sent by a control element assigned to the control device during a movement of the control element from the room containing the medical examination or treatment device, the room communicating with the control device which disables the control operation as a function of the detection result.

12 Claims, 1 Drawing Sheet

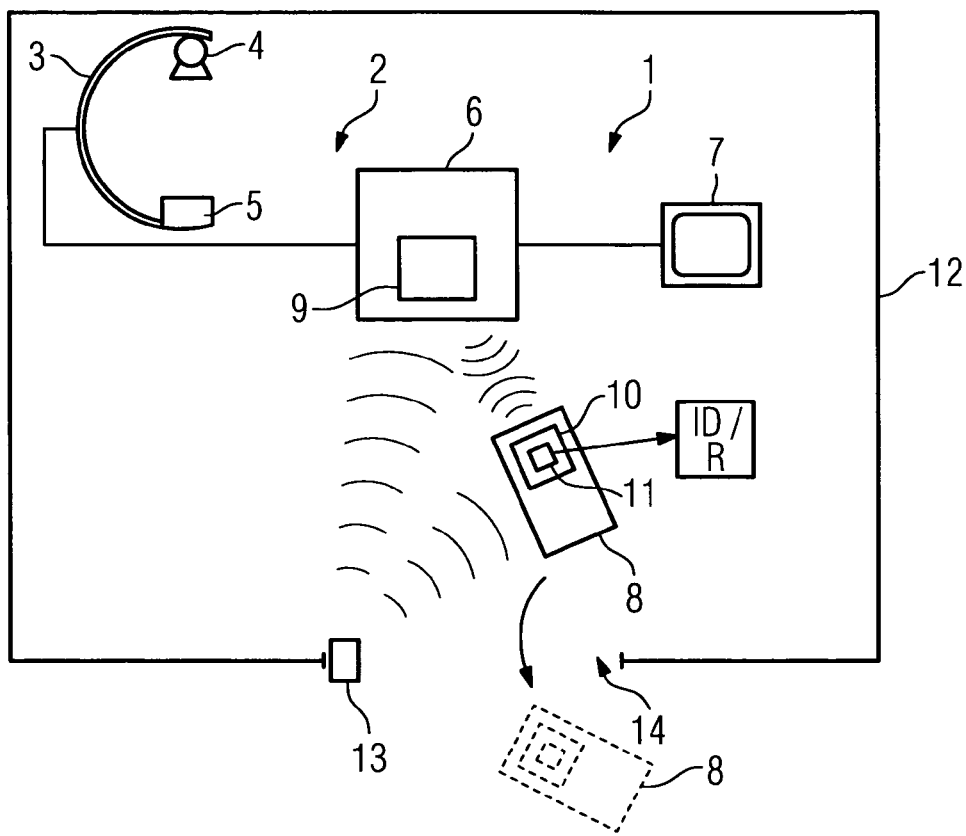
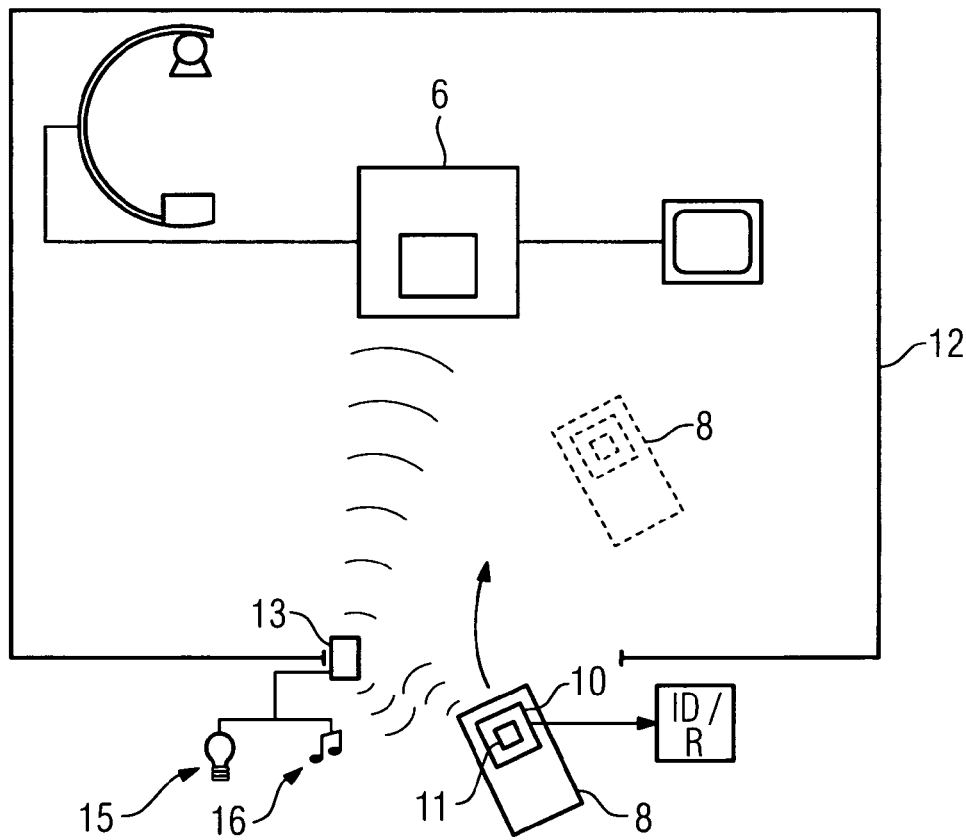

MEDICAL EXAMINATION OR TREATMENT DEVICE, IN PARTICULAR X-RAY OR CT DEVICE

CROSS-REFERENCE TO RELATED APPLICATIONS

This application claims priority to the German Application No. 10 2005 021 604.8, filed May 10, 2005 which is incorporated by reference herein in its entirety.

FIELD OF INVENTION

The invention relates to a medical examination or treatment device, in particular an x-ray or CT device, comprising a control device controlling the operation of one or a number of device elements as well as at least one mobile control element assigned to the control device, said control element wirelessly communicating with the control device in order to operate the examination or treatment device for the purpose of issuing control signals.

BACKGROUND OF INVENTION

Conventional examination or treatment devices, for instance an x-ray system, consist of a number of components separated spatially from one another, such as a patient support table, an x-ray emitter ceiling stand and/or an x-ray emitter floor stand as well as a wall stand or a C-arm. In addition, provision is conventionally made for a control device comprising an image processing facility, with the control device controlling the operation of the device elements to be controlled, in the case of an x-ray device, the generator for instance, which provides the high voltage required for generating x-rays. The examination and/or treatment device is thus operated centrally at the control device which comprises corresponding input options in the form of switches, keys, joysticks etc.

To enable the doctor or the medical personnel to operate at least a part of the device elements to be controlled from another position other than directly on the control device, which is necessary for instance if the doctor or the operating person has to stand directly next to the patient as a result of further parallel examinations, it is known to provide a wireless, mobile function trigger, in the form of a foot switch or a hand switch for instance, which the doctor can move or carry with him. On the one hand, such a wirelessly communicating control element thus allows control to be carried out at a position remote from the control device, but naturally also allows a control if an operator is positioned at the control device, in the case of a foot switch for instance, which communicates wirelessly with the control device.

SUMMARY OF INVENTION

The range of known mobile function triggers generally amounts to a few meters. Within this range, it is ensured that the control device reliably receives the corresponding control signals from the control element assigned to it and can hereby trigger defined functions or suchlike. The possibility of carrying the control element with you, in particular in the case of a mobile hand device, is problematic in that the doctor or the operating person takes the control element with them, goes into another room, in which an x-ray device is located for instance, which is to be operated however using a separate control element assigned to it. This means that mistakes can arise relating to the control element to be used. This can now lead to unwanted functions being activated. The doctor who carries the control element A assigned to the x-ray device A him/herself for instance and who stands in front of the x-ray device B located in the adjacent room for instance and who would like to trigger a function on the x-ray device B, now inadvertently triggers the corresponding function on device A, by virtue of the adequate communication coverage of the control element A, in front of which device A he/she is not positioned, whilst the x-ray device B is not actuated. The doctor is not positioned within the range of vision of the x-ray device A. Unwanted radiation generation and radiation exposition can result there for instance, or the patient support is unintentionally moved for instance.

An object of the invention is thus to design the operation of medical examination or treatment devices which can be operated via mobile, wirelessly communicating control elements, in a more secure manner.

In order to solve this problem, provision is made in accordance with the invention, with a medical examination or treatment device of the type mentioned at the outset, for a detection means to detect an item of information which can be read out and sent from the control element assigned to the control device during a movement of the control element from the room containing the medical examination or treatment device, said room communicating with the control device which disables the control operation as a function of the detection result.

The device according to the invention is characterized by a detection means, with which it is possible to determine if the control element, which is uniquely assigned to the examination or treatment device and/or control device for control communication in the room, is moved out of the room. Once this is determined, a corresponding item of information is issued to the control device by the detection means, said control device then automatically disabling the further control operation at least via the mobile wireless control element. Even if the control element could communicate with the control device from the radio coverage, the control device does not receive or process any control commands coming from the control element as a result of the disabling. In this manner, every unintentional removal of the control element from the room where the device and/or the control device assigned to the control element is located, is inevitably detected and any subsequent communication operation and/or control operation based thereupon is disabled. Faulty operations of an unintentionally removed control element are thus advantageously disabled.

As stated, the detection means is designed to detect a movement of the control element out of the room. It must thus be able to detect the direction of the movement. This is possible for instance by a number of measuring and/or information detections carried out relatively quickly one after another, with the distance of the mobile control element to the stationary detection means being hereby determined and it is possible to detect whether the control element is approaching the detection means, is moving past it or whether it is only being moved within in the room. The detection means provided can be of any nature, it must only be able to reliably detect information which can be read out or is sent from the control element. This information can be written in any element on the control element, in the storage element for instance, which can be read out or is itself able to transmit information in the form of an RFID transponder for instance. In addition, the advantage of such a transponder lies in that certain additional items of information which can be read out at other points can be written in, this being discussed further below.

To further increase safety standards, it is further advantageous if at least one item of identification information which can be read out by the control device or is to be transmitted to the control device for recording the wireless control operation is stored in a storage device of the control element, with the control device comparing the item of identification information with an item of comparison information and the control operation being activated or disabled as a function of the comparison result. A clear assignment between control element and control device and thus examination and treatment device is thus realized in this manner. This is particularly advantageous where a plurality of separate examination or treatment devices with separate control elements are available for instance in different rooms, in a hospital or a large practice. The embodiment according to the invention allows a control element, which is inadvertently removed to be able to readily serve to operate a device located in another room. The identification compared with a specific control device exclusively enables a communication operation, with the number of examination or treatment devices being combined in this case into a system which allows the respective identifications of the individual control elements to be matched to the individual control devices. If the control element A is identified compared with control device A, the networking of the devices excludes the possibility of the same control element A inadvertently identifying itself to the control device D in another room.

It is particularly advantageous if the detection means for detecting the identification information is embodied as the information via which a possible removal of the control element is determined. Within the scope of the identification as well as the inadvertent removal detection, only one single signal, namely the identification signal is used, so that the whole system can be designed to be relatively simple.

Furthermore, the detection means can be configured to detect a backwards movement of the control element in the room as well as to issue an information signal to the control device. If a control element which was previously inadvertently or deliberately removed from the room is brought back into the room after a specific, or optionally parameterizable time span, this is also detected via the detection means. If the control element brought back into the room is the actually assigned control element which, as stated, can be readily derived for instance from the detected identification information, the detection means can correspondingly inform by means of a corresponding signal issuing to the control device, so that this re-activates the control operation via the control element. Until then, the wireless control is in any case disabled as a result of the removal. If another mobile control element of the control device is identified in the meantime as having reported to said control device, the operation can be such that the device operation is possible via this "second" mobile control element, whilst a further control is in any case disabled via the "first" control element in the subsequent period, even if this is brought back into the room with the previously assigned control device for whatever reason.

It is furthermore particularly advantageous if, in the storage device on the control element side, room information which can be read out or transmitted and characterizes the room can be registered in the room in which the medical examination or treatment device and/or the assigned control device is arranged, in particular via the control device or the detection means. The control device and/or the detection means is thus configured as a read and write means, so that a bidirectional data transfer to the control element is possible. By way of example, the control device can already write in the corresponding information characterizing the room in conjunction with the identification of the control element compared with the control device. This information can be read out or transmitted at another point, so that it is possible to detect at any time into which room the control element must be brought back and thus where the assigned device and/or control device is located. This is necessary in larger hospitals with a plurality of different examination or treatment devices for instance, if, as is the usual practice for disinfection purposes, the number of control elements have to be collected, disinfected and subsequently redistributed. A fault-free assignment is readily possible if the respective room into which the control element is to be brought back is read out by each control element.

It is further advantageous if an optical and/or acoustic signal means is assigned to the detection means, said signal means being controllable by the detection means during the detection of another control element assigned to the control device. This embodiment is advantageous in that it is hereby possible to immediately detect during the distribution of the disinfected control elements if a control element is to be inadvertently brought into a room, in which the assigned device is not located. The signal means can be controlled in this way as a function of whether only the identification information is detected by the detection means of instance or additionally also a room information, since a clear assignment of the control element to the respective room is defined via each of these items of information and the correct one as well as a false control element can be detected.

If the control was disabled via the control element by virtue of a detected removal of the control element, this can be resumed as stated if the control element is brought back into the assigned room. To make provision for a further safety step here, it is expedient for the control device or the detection device to be embodied for issuing a request signal to the control element to request the operator to issue a specific response signal via the control element, after a previous disabling of the device operation, with the operation being first activated after a corresponding response signal has been detected. The mobile control operation is only possible when the operator actively issues the response signal by pressing a specific key or suchlike. In other words, an operator action is required for a renewed activation, the operator must actively confirm that the control operation is to be continued using the existing control element.

As stated at the start, the radio coverage of mobile control elements is quite considerable, so that a control element located in another room would still reach the actually assigned control device in terms of communication. In this case, communication with the detection means is naturally also possible. This is now advantageously designed to write in an item of information of the storage device of the control element characterizing the movement of the control element from the room, said item of information being able to be issued to said control element or detection means at least when it is positioned in the communication range to the control device, said control element or detection means being designed to issue a signal which can indicate to the operator how to carry out a treatment triggering the activation of the device operation. If the control element transmits the item of information to the control device or the detection means that it was moved itself from the assigned room, the control device or the detection means sends a corresponding signal back to the control element, at which control element a message "bring control element back into room XYZ" for instance can be output to a suitable display or suchlike, whereby the person who is carrying the control element with him/herself is immediately notified that he/she has inadvertently removed the control element and furthermore contains the information as to where it should be brought back. Once the control element has been brought back, which can be detected via the detection means, device operation can be reactivated and continued.

As already stated, the device or the storage device on the control element side is preferably an RFID transponder. It can be any type of device which is able to store the corresponding item or information or the corresponding signal in a readable manner or to actively send it itself, depending on how the embodiment is selected. The control device and the detection means are designed according to the embodiment of this device on the control element side, preferably as a read and/or write device, depending on whether a reading operation or also additionally an active writing operation is to be realized.

BRIEF DESCRIPTION OF THE DRAWINGS

Further advantages, disadvantages and details of the invention emerge from the exemplary embodiments described below, as well as with reference to drawings, in which;

FIG. 1 shows a schematic diagram of a medical examination or treatment device, with the mobile control element moving out of the room, and FIG. 2 shows a diagram according to FIG. 1, with the mobile control element being moved back into the room.

DETAILED DESCRIPTION OF INVENTION

FIG. 1 shows a medical examination or treatment device 1 according to the invention in the form of an x-ray device 2 comprising a C-arm 3 with a radiation source 4 connected thereto and a radiation receiver 5 as well as a control device 6 controlling the movement of the C-arm as well as the operation of the image exposure, said control facility 6 having integrated image processing (not shown in further detail) as well as a monitor 7 for image output assigned thereto. The control device 6, which can be controlled manually directly on site via an operator panel (not shown in further detail), is further assigned a mobile control element 8, in the form of a hand-held terminal for instance, which communicates wirelessly with the control facility 6. For this purpose, the control device 6 comprises a communication device, in particular a combined transmitting and receiving device 9 and the control element 8 comprises a corresponding communication device at least in the form of a transmitting device 10.

To enable the x-ray device 2 to be controlled remotely via the control element 8, the control element 8 is first identified to the control facility 6. For this purpose, provision is made in the control element 8 for a storage device 11, in which storage device 11 an item of identification information is stored, which is labeled in the enlarged box marked as "ID". This item of identification information is transmitted to the control device 6 and/or its transmitting and/or receiving device 9 via the transmitting device 10 and is stored there and if necessary compared with an existing item of comparison information. In each case, a unique device-specific assignment of the control element 8 to the control device 6 and/or to the x-ray device 2 is carried out, which permits the control device 6 to be operated exclusively via precisely this control element 8. The control device is actually only activated after the information comparison has been identified and/or assigned and if necessary implemented, so that the wireless remote control operation is possible.

Within the scope of this communication it is further possible to transmit an item of room information to the control element 8, said room information tangibly specifying in which room 12 the x-ray facility 2 is arranged, and from there a communication device designed as a combined transmitting and receiving device is received, where it is written to the storage device 11. This storage device can be an RFID transponder for instance which can be written and read in a reversible fashion.

After this identification procedure has been implemented, provision is made for a unique device assignment on the one hand and on the other hand a unique room identification of the control element by transmitting the room information, which is shown in the enlarged box by "R".

Provision is furthermore made for a detection means 13, which is arranged in the region of the door 14 of the room 12. If the control element 8 is inadvertently moved out of the room by the operator after a recording procedure has terminated, as shown by the arrow, this is detected via the detection means 13 which is able to directionally determine the movement of the control element. This can result in the detection means 13 reading out the content of the storage device 11, or the control element 8 continually transmitting an information signal, the identification signal "ID" for instance, which is detected by the detection means 13 configured as a transmitting and receiving means or a reading and writing device 13. Once it is determined via the detection means 13 that the control element 8 is moved out of the room, as is shown with a dashed line, the detection means wirelessly provides a corresponding item of information to the control facility 6, which thereupon disables the further control operation via the control element 8 thereby rendering a remote control no longer possible. Nevertheless, the x-ray device 2 can naturally be operated via the control devices directly coupled to the control device 6. This ensures that in the case that the control element 8 is carried for instance into the adjacent room and inadvertently used there for operating a device located therein, a faulty operation of the x-ray device 2 located in the room 1, said x-ray device being in the communication range, is avoided.

The optionally transmitted room information "R" can be read out by means of a corresponding reading means at any point. It is hereby possible to always find out about the room into which the control element 8 is to be brought back. If all mobile control elements are brought together for joint disinfection purposes, as is usual in larger hospitals for instance, the corresponding room information can be read out by each control element 8 for subsequent reverse distribution, so that the correct control element 8 can be brought back into the correct room.

It is furthermore possible that if the control element 8 is moved out of the room 12, a corresponding item of information which identifies this is written into the storage device 11 via the detection means 13. An indicator can be directly triggered on a corresponding display on the control element 7 via this item of information for instance, said indicator pointing out to the operator that he has inadvertently removed the control element 8 and asks him to bring it back into the room 12 without delay or suchlike. It is also conceivable that the detection means 13 reads out this information when the remote control element 8 is brought back into the vicinity of the room 12 and a signal is sent to the control element 8, which notifies to the operator to bring the control element 8 back into the room 12 or suchlike. This ensures in different manners that the operator is informed for instance that he is taking the control element 8 with him, but is to bring it back into the room 12.

FIG. 2 shows the reverse case, if namely the control element 8 brought out of the room is brought back into the room. Once the control element 8 approaches the detection means 13, this detects the identification information ID for instance, reads this out or receives the identification signal actively sent by the control element 8. On the basis of this identification signal, it can either be detected via the detection means 13 that the "correct" control element is involved, alternatively the room information "R" written in where necessary can naturally be read out and compared by the detection means. If one or both items of information read out and received correspond with one another, it is clear that the "correct" control element 8 is involved. This can then be brought back into the room 12.

In order now to be able to resume the wireless control operation, different options are conceivable. It is possible on the one hand that the detection means 13 provides a corresponding item of information to the control device 6, which indicates that the "correct" control element is once again in the room, so that the control device 6 is immediately activated. Alternatively, it is also conceivable that either the detection means 13 or the control device 6 transmit a signal to the control element 8, which receives this and results in an indicator being issued to the operator which asks him to press a certain confirmation key or to carry out a specific action such as pressing a certain key combination or the like, so as to introduce further safety steps. The control device 6 can only be activated when the operator has actively carried out this required action, with a wireless control operation is then being possible again. It is naturally also conceivable that in addition to detecting the corresponding information about the detection means 13, the control device 6 once again reads out the corresponding one or two items of information, compares them and once again verifies the control element 8.

If the "correct" control element 8 is not involved, this is recognized on the basis of the identification information "ID" and/or the room information "R" detected by the detection means 13. Optical or acoustic signal means 15,16 are assigned to the detection means 13, said signal means 15,16 immediately being activated via the detection means 13. This signal means, for instance flashing lights or alarms, immediately signals to the operator that this is not the correct control element 8 which he would like to bring back into the room 12. Such an error can arise for instance with a renewed distribution of cleaned control elements and can be immediately recognized.

The invention claimed is:

1. A medical examination or treatment device arranged in an examination room and having a plurality of device components, said medical examination or treatment device comprising:
   a control device for controlling at least one of the device components;
   at least one mobile control element configured to communicate wirelessly with the control device for remotely operating the device component via control signals sent to the control device, the mobile control element further configured to generate a message upon the mobile control element leaving the examination room, the message including information on the mobile control element's leaving the examination room; and
   a detector element connected to the control device for reading the message and for blocking the device component upon reading the message.

2. The medical examination or treatment device according to claim 1, wherein the mobile control element is further configured such that the message includes information identifying the respective device component which is currently controlled by the mobile control element.

3. The medical examination or treatment device according to claim 1, wherein the message is stored in a memory of the mobile control element and further includes control information for enabling the remote operation of the examination or treatment device via the mobile control element.

4. The medical examination or treatment device according to claim 3, wherein the control device is further configured to compare the message to a default lookup message such that the remote operation of the examination or treatment device via the mobile control element can be enabled and blocked based upon the comparison.

5. The medical examination or treatment device according to claim 2, wherein the message is used for identifying the respective device component currently controlled by the mobile control element and for detecting the mobile control element's leaving the examination room such that the control device is configured to both determine which of the device components is to be controlled by the mobile control device and if such device component needs to be blocked, the determination based solely on the message.

6. The medical examination or treatment device according to claim 1, wherein the detector element is further configured to detect a movement of the control element within the examination room and for transmitting a movement signal having information on the detected movement to the control device.

7. The medical examination or treatment device according to claim 3, wherein the control device or the detector element is configured to write room identification into the memory, the room identification information identifying the examination room.

8. The medical examination or treatment device according to claim 7, wherein the detector element has an optical or acoustic signal generator and is further configured to detect a presence of a further mobile control element which is not assigned to the control device, the detected presence of the further mobile control element indicated by the optical or acoustic signal generator.

9. The medical examination or treatment device according to claim 1, wherein the control device or the detector element is further configured to transmit a request signal to the mobile control element, the request signal prompting an operator to transmit a response signal via the mobile control element, the request signal transmitted upon blocking the device component, and the response signal configured to release the device component for further control by the mobile control element.

10. The medical examination or treatment device according claim 3, wherein the message is stored in the memory, the mobile control element further configured to transmit the stored message to the detection element or to the control device if the mobile control element is arranged within a communication range of the control device.

11. The medical examination or treatment device according claim 10, wherein the control device is further configured to transmit an information signal to an operator, the information signal indicating to the operator that a release of the device component is necessary.

12. The medical examination or treatment device according claim 10, wherein the memory includes an RFID transponder.

* * * * *